United States Patent [19]

Warriner

[11] Patent Number: Plant 7,542

[45] Date of Patent: Jun. 4, 1991

[54] ROSE PLANT BARBARA BUSH

[75] Inventor: William A. Warriner, Tustin, Calif.

[73] Assignee: Bear Creek Gardens, Inc., Medford, Oreg.

[21] Appl. No.: 568,661

[22] Filed: Aug. 20, 1990

[51] Int. Cl.[5] ..... A01H 5/00

[52] U.S. Cl. ..... Plt./18

[58] Field of Search ..... Plt./18, 11, 19

[56] References Cited

U.S. PATENT DOCUMENTS

| | | | |
|---|---|---|---|
| P.P. 2,053 | 4/1961 | Dean | Plt. 11 |
| P.P. 3,431 | 1/1974 | Warriner | Plt. 11 |
| P.P. 3,997 | 12/1976 | Warriner | Plt. 11 |
| P.P. 4,440 | 7/1979 | Delbard | Plt. 18 |
| P.P. 4,707 | 5/1981 | Swim et al. | Plt. 18 |
| P.P. 6,599 | 2/1989 | Ohkawra | Plt. 18 |
| P.P. 7,129 | 1/1990 | Warriner | Plt. 18 |

*Primary Examiner*—James R. Feyrer

*Attorney, Agent, or Firm*—Klarquist, Sparkman, Campbell, Leigh & Whinston

[57] ABSTRACT

Hybrid tea rose characterized by excellent exhibition flower form, very vigorous upright growth habit, high garden flower production, photosensitivity in the flowers, sepals, receptacles and peduncles, and a light fruity fragrance.

1 Drawing Sheet

1

This present invention relates to a new and distinct variety of rose plant of the hybrid tea class which was originated by me by crossing the variety Pristine, U.S. Plant Pat. No. 3,997, with the variety Antigua, U.S. Plant Pat. No. 3,431.

The primary objective of this breeding was to produce a new rose variety having the bud and flower form of Pristine coupled with the increased flower production of Antigua. The objective was substantially achieved along with other desirable improvements as evidenced by the following unique combination of characteristics which are outstanding in the new variety and which distinguish it from its parents, as well as from all other varieties of which I am aware:

1. Excellent exhibition flower form.
2. Very vigorous upright growth.
3. High garden flower production.
4. Photosensitivity in the flowers, sepals, receptacle, and peduncle.
5. A light fruity fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with the Royal Horticultural Society Colour Chart, except where ordinary dictionary significance of color is indicated.

Parentage:

*Seed parent.*—Pristine, U.S. Plant Pat. No. 3,997.

*Pollen parent*—Antigua, U.S. Plant Pat. No. 3,431.

Classification:

*Botanical.*—*Rosa hybrida.*

*Commercial.*—Hybrid Tea.

2

FLOWER

Observations made from specimens grown in a garden in Somis, Calif., in July, 1990.

Blooming habit: Recurrent.

Bud:

*Size.*—1½ inches when the petals start to unfurl.

*Form.*—Long, pointed ovoid.

*Color.*—When sepals first divide: Red Group 38A. When half blown, the upper sides of the petals are: Red Group 39B on the petal edges. This color changes to Red Group 39C to D toward the center of the flower; and the lower sides of the petals are: The guard petals are Red Group 39B but change to Red Group 39C to D towards the petal base. The inner petal lower sides which have not been exposed to the sun are Red Group 39D.

*Sepals*—Color: Green Group 39B but with a reddish maroon blush (close to Red Group 53B). Surface texture: Covered with fine hairs. There are three normally appendaged sepals. There are two unappendaged sepals with hairy edges.

*Receptacle.*—Color: The receptacle color is: Green group 137C but with a reddish maroon blush (Red Group 538). Shape: Funnel. Size: Medium 3/16 inch × ¼ inch. Surface: Smooth with occasional hairs.

*Peduncle.*—Length: Short 1½ inches to 1¾ inches. Surface: Rough, prickly. Color: Medium green but bronzy where exposed to the sun. Strength: Stiff, erect.

Bloom:

*Size.*—Large. Average open size is 4½ inches.

*Borne.*—Singly or several together in open clusters. If in clusters: Pyramidal.

*Stems.*—Medium.

*Form.*—When first open: High centered. Permanence: Retains its form to the end, outer petals curl back.

*Petalage.*—Number of petals under normal condition: 35–40.

*Color.*—The upper side of the petals is: Red Group 39A on petal edges changing to Red Group 39B to 39C. The reverse side of the petals is: Same on guard petals. Inner petals are all Red Group 39D. The base of petals is: Yellow half moon at petal base about ¼ inch by ¼ inch size. The major color on the upper side is: Red Group 39C.

*Variegations.*—None.

*Discoloration.*—The general tonality at the end of the first day: None. At the end of the third day: Intensification of color on petal margins. The Red Group 39A expands in area as more petal surface gets exposed to the sun.

*Fragrance.*—Moderate, fruity.

Petals:

*Texture.*—Thick but very smooth.

*Shape.*—Round.

*Form.*—Tips slightly recurved.

*Arrangement.*—Imbricated. Petaloids in the center: Few.

*Persistence.*—Drop off cleanly.

*Lastingness.*—On the plant: Long, 5 days in warm weather, 7 days if the weather is cool. As a cut flower: Long, 7 days.

Reproductive parts:

*Anthers.*—Size: Medium. Quantity: Many. Color: Yellow. Arrangement: Regular around styles.

*Filaments.*—Color: Redish brown.

*Pollen.*—Color: Lemon yellow.

*Styles.*—Color: Red.

*Stigmas.*—Color: Greenish white.

Form: Bush.

Growth: Very vigourous, upright, branching.

Foliage:

*Size.*—Large, 6 to 6½ inches long, 4 inches wide.

*Quantity.*—Abundant.

*Color.*—New foliage: Reddish bronze. Old foliage: Dark green— Green Group 137B.

Leaflets: Number of leaflets on normal mid-stem leaves: 5 to 7.

*Shape.*—Pointed oval.

*Texture.*—Upper side: Leathery, glossy.

*Edge.*—Serrated.

*Serration.*—Single, small.

*Petiole rachis.*—Color: Reddish on upper side, green lower side.

*Petiole underside.*—Rough with prickles.

*Stipules.*—Long, ¾ inch to 1 inch, bearded.

*Disease resistance.*—Susceptible to mildew/black-spot under normal growing conditions at Somis, Calif., but resistant to rust.

Wood:

*New Wood.*—Color: Reddish. Bark: Smooth.

*Old Wood.*—Color: Green. Bark: Smooth.

Prickles:

*Quantity.*—On main canes from base: Many. On laterals from main canes: Many.

*Form.*—Short, less than ¼ inch long, hooked downward.

*Color when young.*—Red.

Small prickles:

*Quantity.*—On main stalks: Few. On laterals: Many.

*Color.*—Green, brown.

I claim:

1. A new and distinct variety of rose plant of the hybrid tea class, substantially as herein shown and described, characterized particularly as to novelty by the unique combination of its deep coral pink color on petal margins that softens in the flower center, its vigorous and high flower production, light fruity fragrance, reddish-maroon peduncles, sepals and receptacle, wherever these have been exposed to sunlight.

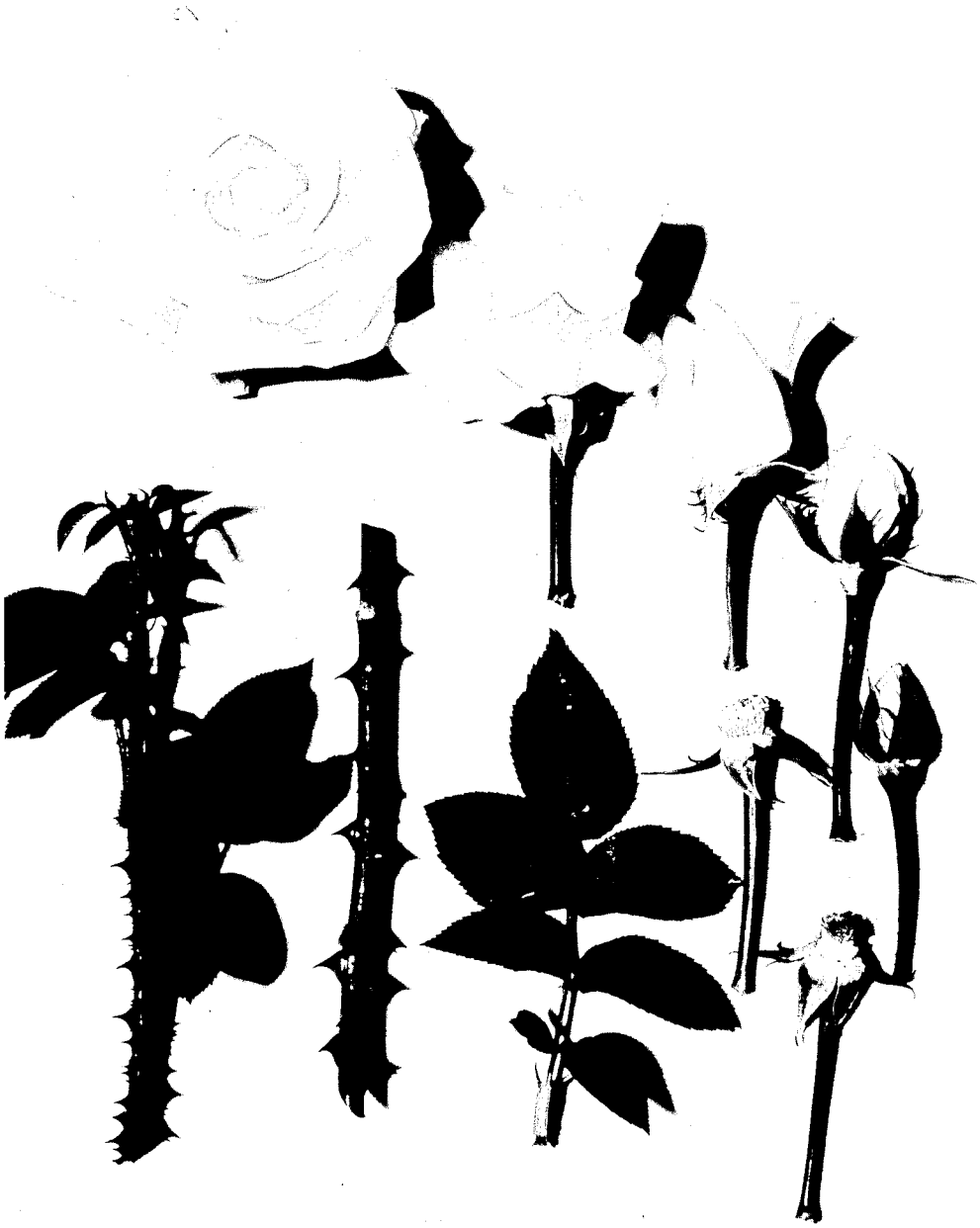

* * * * *